US00RE46183E

(19) United States
(12) Reissued Patent
Arthun

(10) Patent Number: US RE46,183 E
(45) **Date of Reissued Patent: *Oct. 25, 2016**

(54) SEALING APPLIANCE

(75) Inventors: Nils Arthun, Sandnes (NO); Liv Arthun, legal representative, Sandnes (NO)

(73) Assignee: Merck Chemicals and Life Science AB, Solna (SE)

( * ) Notice: This patent is subject to a terminal disclaimer.

(21) Appl. No.: 13/613,669

(22) Filed: Sep. 13, 2012
(Under 37 CFR 1.47)

Related U.S. Patent Documents

Reissue of:
(64) Patent No.: 6,779,575
Issued: Aug. 24, 2004
Appl. No.: 09/701,459
PCT Filed: May 25, 1999
PCT No.: PCT/SE99/00878
§ 371 (c)(1),
(2), (4) Date: Dec. 4, 2000
PCT Pub. No.: WO99/64837
PCT Pub. Date: Dec. 15, 1999

(30) Foreign Application Priority Data

May 28, 1998 (SE) ..... 9801885

(51) Int. Cl.
*B29C 65/00* (2006.01)
*A61M 39/14* (2006.01)

(52) U.S. Cl.
CPC ..... *B29C 66/857* (2013.01); *A61M 39/146* (2013.01)

(58) Field of Classification Search
None
See application file for complete search history.

(56) References Cited

U.S. PATENT DOCUMENTS

| | | | |
|---|---|---|---|
| 2,776,473 | A | 1/1957 | Dailey et al. |
| 3,175,556 | A | 3/1965 | Wood et al. |
| 3,263,465 | A | 8/1966 | Way et al. |
| 3,276,447 | A | 10/1966 | Hamilton |
| 3,523,351 | A | 8/1970 | Filia |

(Continued)

FOREIGN PATENT DOCUMENTS

| | | | |
|---|---|---|---|
| EP | 0508474 | 10/1992 | ..... B29C 65/20 |
| EP | 0508474 A2 | 10/1992 | |

(Continued)

OTHER PUBLICATIONS

Office Action mailed Sep. 20, 2012 in corresponding U.S. Appl. No. 12/422,820.

(Continued)

*Primary Examiner* — George Koch
(74) *Attorney, Agent, or Firm* — Hamilton, Brook, Smith & Reynolds, P.C.

(57) ABSTRACT

An appliance for sealing elastic hoses with a sleeve, which is plastically deformable and slipped onto the hose, has two jaws which are movable towards and away from each other. One jaw has two straight bars which project towards the other jaw and extend transversely of the sleeve to make two transverse indentations in the sleeve and the hose when the jaws are moving towards each other. The same jaw has a cutting edge which projects towards the other jaw and is directed transversely of the sleeve, the cutting edge making a substantially transverse cutting indication in the sleeve and the hose when the jaws are moving towards each other.

16 Claims, 5 Drawing Sheets

(56) References Cited

U.S. PATENT DOCUMENTS

| | | | | | |
|---|---|---|---|---|---|
| 3,576,122 | A | | 4/1971 | Churla | |
| 3,931,671 | A | | 1/1976 | Dittmann | |
| 4,026,294 | A | | 5/1977 | Mattler | |
| 4,428,374 | A | | 1/1984 | Auburn | |
| 4,608,178 | A | * | 8/1986 | Johansson et al. | 210/744 |
| 4,625,494 | A | | 12/1986 | Iwatschenko et al. | |
| 4,637,242 | A | * | 1/1987 | Undin et al. | 72/410 |
| 5,105,648 | A | | 4/1992 | Steiner et al. | |
| 5,131,213 | A | | 7/1992 | Shanklin et al. | |
| 5,236,331 | A | | 8/1993 | Liu | |
| 5,300,060 | A | * | 4/1994 | Nelson | 604/410 |
| 5,509,291 | A | | 4/1996 | Nilsson et al. | |
| 5,520,218 | A | | 5/1996 | Hlavinka et al. | |
| 5,584,840 | A | | 12/1996 | Ramsey et al. | |
| 5,649,444 | A | | 7/1997 | Nilsson et al. | |
| 5,711,078 | A | | 1/1998 | Patton et al. | |
| 5,732,530 | A | * | 3/1998 | Pfaff | 53/403 |
| 5,768,935 | A | * | 6/1998 | Owens | 72/416 |
| 5,775,158 | A | * | 7/1998 | Hensley et al. | 30/180 |
| 5,968,054 | A | | 10/1999 | Yeatts, II et al. | |
| 6,230,781 | B1 | | 5/2001 | Smith | |
| 6,779,575 | B1 | | 8/2004 | Arthun | |
| RE41,169 | E | | 3/2010 | Arthun | |
| 7,959,754 | B2 | | 6/2011 | Arthun | |
| 2008/0149503 | A1 | | 6/2008 | Pandori | |
| 2011/0197426 | A1 | | 8/2011 | Arthun | |

FOREIGN PATENT DOCUMENTS

| | | | | |
|---|---|---|---|---|
| WO | 97/16715 | A1 | 5/1997 | |
| WO | 9716715 | | 5/1997 | G01N 1/10 |
| WO | 99/64837 | A1 | 12/1999 | |

OTHER PUBLICATIONS

Case 2:05-cv-05175-DMC-MF, Document 35, US District Court for the District of New Jersey, Filed Jun. 3, 2010; 37-Pages; "Gore's Memorandum in Opposition to Millipore's Motion to Reopen The Action and for Contempt and Millipore's Motion to Substitute".
Case 2:05-cv-05175-DMC-MF, Document 23-1, US District Court for the District of New Jersey, Filed May 12, 2010; 22-Pages; "Memorandum in Support of Motion to Reopen the Action for the Limited Purpose of Enforcing the Consent Judgment Order and for Contempt Against W.L. Gore & Associates, Inc."
Case 2:05-cv-05175-DMC-MF, Document 43, US District Court for the District of New Jersey, Filed Jun. 14, 2010; 23-Pages; "Plaintiffs' Reply to Defendant's Opposition to Motion to Reopen the Action for the Limited Purpose of Enforcing the Consent Judgment Order and for Contempt Against W.L. Gore & Associates, Inc."
Civil Action No. 2:11-cv-01453-ES-CLW, US District Court for the District of New Jersey, Gore's Invalidity Contentions, dated May 25, 2012, 20 pages.
Civil Action No. 2:11-cv-01453-ES-CLW, US District Court for the District of New Jersey, Gore's Invalidity Contentions, dated May 25, 2012, Exhibit A, 35 pages.
Civil Action No. 2:11-cv-01453-ES-CLW, US District Court for the District of New Jersey, Gore's Invalidity Contentions, dated May 25, 2012, Exhibit B, 38 pages.
Civil Action No. 2:11-cv-01453-ES-CLW, US District Court for the District of New Jersey, Gore's Invalidity Contentions, dated May 25, 2012, Exhibit C, 33 pages.
Civil Action No. 2:11-cv-01453-ES-CLW, US District Court for the District of New Jersey, Gore's Invalidity Contentions, dated May 25, 2012, Exhibit D, 37 pages.
Office Action dated Mar. 10, 2010 in corresponding U.S. Appl. No. 12/422,820.
Final Rejection dated Nov. 16, 2010 in corresponding U.S. Appl. No. 12/422,820.
Office Action mailed Aug. 10, 2011 in corresponding U.S. Appl. No. 12/422,820.
Notice of Allowance mailed Apr. 11, 2012 in corresponding U.S. Appl. No. 12/422,820.
Final Rejection mailed Apr. 16, 2013 in corresponding U.S. Appl. No. 12/422,820.
Office Action mailed Apr. 5, 2013 in corresponding U.S. Appl. No. 13/613,658.
Office Action mailed Mar. 19, 2013 in corresponding U.S. Appl. No. 131536,199.
International Search Report mailed Sep. 7, 1999 in PCT application No. PCT/SE99/00878.
International Preliminary Exam Report mailed Sep. 26, 2000 in PCT application No. PCT/SE99/00878.
Civil Action No. 2:05-05175 (DMC/MF), USDC for the District of New Jersey, "Consent Judgment Order", Document 22, Filed Feb. 28, 2007, 5 pages.
Civil Action No. 2:05-05175 (DMC/MF), USDC for the District of New Jersey, "Opinion" (granting substitution of parties, denying motion for contempt), Document 50, Filed Dec. 29, 2010, 13 pages.
Civil Action No. 2:05-05175 (DMC/MF), USDC for the District of New Jersey, "Exhibit A, Exhibit B, Exhibit C", Exhibits referenced in Document 50, Filed Dec. 29, 2010, 3 pages.
Civil Action No. 2:11-cv-01453-DMC-JAD, USDC for the District of New Jersey, "Memorandum of Law in Support of Application for Preliminary Injunction", Document 4-1, Filed Mar. 15, 2011, 26 pages.
Civil Action No. 2:11-cv-01453-DMC-JAD, USDC for the District of New Jersey, "Gore's Opposition to Millipore's Application For Preliminary Injunction", Document 20, Filed Apr. 15, 2011, 37 pages.
Civil Action No. 2:11-cv-01453-DMC-JAD, USDC for the District of New Jersey, "Expert Report of James Dean Vogel", Document 20-9, Filed Apr. 15, 2011, 14 pages.
Civil Action No. 2:11-cv-01453-DMC-JAD, USDC for the District of New Jersey, "Millipore's Reply to Gore's Opposition to Application for Preliminary Injunction", Document 21, Filed Apr. 27, 2011, 17 pages.
Civil Action No. 2:11-cv-01453-DMC-JAD, USDC for the District of New Jersey, "Supplemental Declaration of Samir Nayfeh", Document 21-1, Filed Apr. 27, 2011, 17 pages.
Civil Action No. 2:11-cv-01453-ES-CLW, USDC for the District of New Jersey, "Opinion" (denying Motion for Preliminary Injunction), Document 33, Filed Nov. 9, 2011, 26 pages.
Civil Action No. 2:11-cv-01453-DMC-JAD, USDC for the District of New Jersey, "Disclosure of Asserted Claims and Infringement Contentions", Filed Jun. 30, 2011, 40 pages.
Civil Action No. 2:11-cv-01453-ES-CLW, USDC for the District of New Jersey, "Gore's Non-Infringement Contentions and Responses to Millipore's Infringement Contentions", Filed Aug. 15, 2011, 26 pages.
Civil Action No. 2:11-cv-01453-ES-CLW, USDC for the District of New Jersey, "Gore's Response Claim Construction Brief", Document 42, Filed Feb. 8, 2012, 32 pages.
Civil Action No. 2:11-cv-01453-ES-CLW, USDC for the District of New Jersey, "Millipore's Responding Markman Brief", Document 43, Filed Feb. 8, 2012, 29 pages.
Civil Action No. 2:11-cv-01453-ES-CLW, USDC for the District of New Jersey, Relevant pages of W.L. Gore & Associates, Inc.'s Answers to Millipore's Second Set of Interrogatories (Interrogatory Nos. 10-12), Served Jul. 2, 2012, 7 pages.
Civil Action No. 2:11-cv-01453-ES-CLW, USDC for the District of New Jersey, "Opinion" (on claim construction), Document 82, Dated Oct. 24, 2012, 22 pages.
Civil Action No. 2:11-cv-01453-ES-CLW, USDC for the District of New Jersey, Relevant page of "Pull-off test post cut, half inch and three quarter-tubing size Test protocol", bearing Bates No. MNJ0296286, Oct. 31, 2006, 1 page.
Civil Action No. 2:11-cv-01453-ES-CLW, USDC for the District of New Jersey, Relevant page of "Use-life integrity test post cut Novaseal quarter and half inch tubing size Test protocol", bearing Bates No. MNJ0311874, Jan. 25, 2007, 1 page.
Civil Action No. 2:11-cv-01453-ES-CLW, USDC for the District of New Jersey, "Statement of Use under 37 CFR 2.88 with Declaration" from US Trademark application 75/066,270, executed Jan. 27, 1998, bearing Bates Nos. WLG-NJ00053431-32, 2 pages.
Civil Action No. 2:11-cv-01453-ES-SCM, USDC for the District of New Jersey, "Stipulated Order of Dismissal With Prejudice", Document 86, Issued Jun. 10, 2013 and Filed Jun. 13, 2013, 2 pages.

* cited by examiner

SEALING APPLIANCE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*This application is a continuation reissue application of U.S. patent application Ser. No. 12/422,820, which is a divisional reissue application of U.S. patent application Ser. No. 11/305,813, filed Dec. 19, 2005, now U.S. Pat. No. Re. 41,169, which is a reissue application of U.S. Pat. No. 6,779,575, issued on Aug. 24, 2004, which was a national stage application of PCT/SE99/00878, filed May 25, 1999, which claims priority to SE-9801885, filed May 28, 1998, the disclosures of which are herewith incorporated by reference in their entirety.*

*More than one reissue application has been filed for the reissue of U.S. Pat. No. 6,779,575. The reissue applications are application Ser. No. 11/305,813, filed Dec. 19, 2005 (the original reissue application); application Ser. No. 12/422,820, filed Apr. 13, 2009, which is a divisional reissue of Ser. No. 11/305,813; application Ser. No. 12/422,835 (now U.S. Pat. No. 7,959,754), filed Apr. 13, 2009, which is a divisional reissue of application Ser. No. 11/305,813; application Ser. No. 13/092,522, filed Apr. 22, 2011 (abandoned); application Ser. No. 13/536,199, filed Jun. 28, 2012, which is a continuation reissue of application Ser. No. 12/422,820; application Ser. No. 13/613,669 (the present application), filed Sep. 13, 2012, which is a continuation reissue of application Ser. No. 12/422,820; and application Ser. No. 13/613,658, filed Sep. 13, 2012, which is a continuation reissue of application Ser. No. 12/422,820.*

TECHNICAL FIELD

The present invention relates to an appliance for mechanical sealing of hollow hoses of elastic material with a sealing means which is made of plastically deformable material and which is applied to the hose, said appliance having two jaws, which are movable towards and away from each other and which, when moving towards each other, crimp the sealing means against the hose to seal the same.

BACKGROUND OF THE INVENTION

In a prior-art sealing appliance of the type mentioned by way of introduction, the sealing means in the form of a folded clip is applied to a likewise folded end of the hose. The clip is then crimped against the hose to seal the same, after which the hose is cut downstream of the clip by means of a pair of scissors or some other cutting tool.

As the relevant hoses have a relatively small diameter, say 5-10 mm, the clips are also relatively small and often difficult to apply in the right position on the folded end of the hose. Nor is it infrequent that the clip falls off the end of the hose, before the sealing appliance has managed to grip it for crimping against the hose with the ensuing risk of sealing not taking place.

The sealing appliance according to the invention is primarily to be used in the type of device which is intended for introduction and/or withdrawal of a medium in a container and which is disclosed and described in WO 97/16715. More specifically, it is intended for contamination-free sealing and cutting of the hoses which extend between the conveying means and the collecting vessels which are connected to the process container, so that the collecting vessels after being filled with a medium from the process container can be moved without any risk of contamination to a laboratory or the like for sampling or analysis of the medium.

In the above use of the sealing appliance, which requires good hygienic conditions and contamination-free environment/surroundings, clips of the mentioned type are unacceptable. One reason for this is that they are difficult to handle and often do not provide the desired sealing. Another reason is that there is in most cases at least a small portion of the hose left downstream of the clip containing a small quantity of the medium which leaks out to the surrounding area with an obvious risk of contamination.

OBJECT OF THE INVENTION

The main object of the present invention is to provide a sealing appliance of the type mentioned by way of introduction, satisfying all the requirements for contamination-free transport of the relevant collecting vessels, which are filled with a medium, to the laboratory or the like.

SUMMARY OF THE INVENTION

This as well as related objects are achieved in a simple and efficient manner in that the sealing means has the form of a sleeve which is slipped on to the hose, that at least one of the jaws has at least one bar which projects towards the other jaw and which, when the jaws are moving towards each other, makes an indentation in the sleeve and the hose to reinforce the sealing thereof as well as the fixing of the sleeve on the hose, and that at least one of the jaws has a cutting means, which projects towards the other jaw and which, when the jaws are moving towards each other, makes a cutting indication in the sleeve and the hose to allow a sealing cutting of the hose.

In a particularly preferred embodiment there are at least two straight bars which are arranged substantially in parallel at a distance from each other and extend substantially transversely of the longitudinal direction of the sleeve to make a corresponding number of substantially transverse indentations in the sleeve and the hose, the cutting means preferably extending substantially transversely of the longitudinal direction of the sleeve and making a substantially transverse cutting indication in the sleeve and the hose.

BRIEF DESCRIPTION OF THE DRAWINGS

The invention will be described below in more detail with reference to the accompanying drawings, in which.

DESCRIPTION OF A PREFERRED EMBODIMENT

Figure 1:
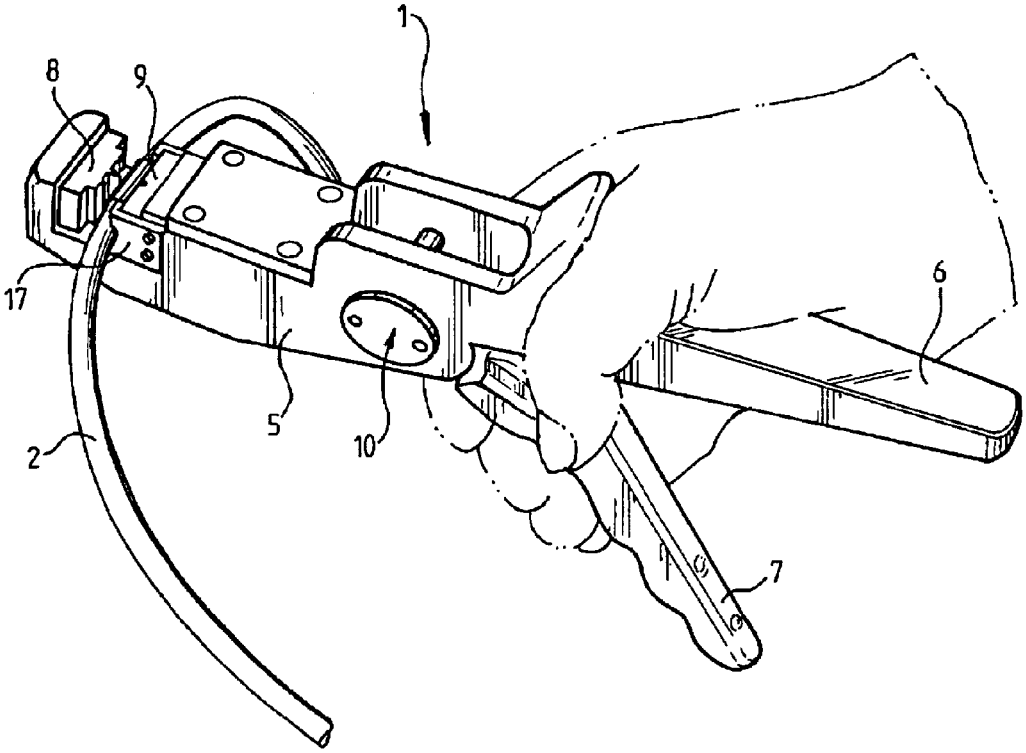
FIG. 1 is a perspective view, seen obliquely from above, of an appliance according to a currently particularly preferred embodiment of the invention in an initial position for the sealing of a hose.

As mentioned above, the appliance generally designated 1 is primarily conceived for use in the type of device which is intended for introduction and/or withdrawal of a medium in a container and which is disclosed and described in WO 97/16715. More specifically, it is intended for sealing and cutting the hoses in a mechanical and contamination-free manner, which extend between the conveying means and the collecting vessels which are connected to the process container, so that the collecting vessels after being filled with a medium from the process container can be transported without any risk of contamination to a laboratory or the like for sampling or analysis of the medium.

Still, the appliance 1 can, of course, also be used in a number of other applications where good hygienic conditions and/or contamination-free surroundings and/or working environment are required to a varying extent.

Thus the appliance 1 is generally intended for mechanical sealing of hollow hoses 2 of elastic material, e.g. rubber or plastic, of a quality which is suitable for the purpose. The sealing is carried out with the aid of a sealing means 3, which is made of a plastically deformable material, e.g. plastic or metal, having suitable plastic properties and which is applied to the hose 2. In the preferred embodiment shown, the sealing means 3 consists of a metal sleeve 4 which has been slipped on to the hose 2 in advance. The sleeve has a length of preferably two or more multiples of the diameter of the hose 2, which in turn is typically in the range of 5-10 mm.

Figure 3:
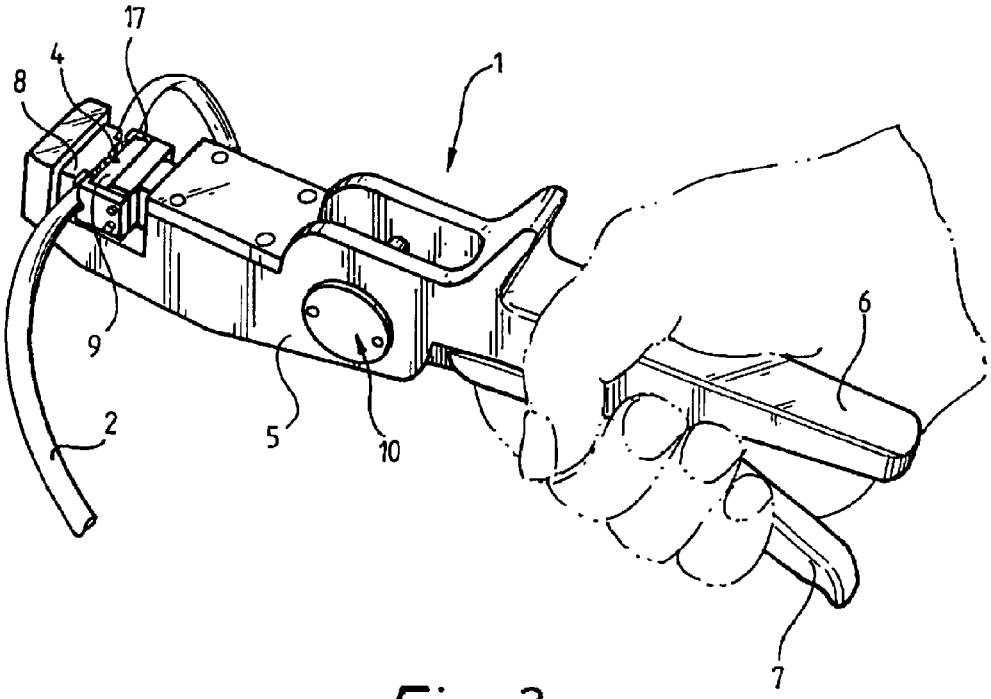
FIG. 3 is a perspective view of the appliance corresponding to FIG. 1 in end position of the sealing.

As shown in FIGS. 1 and 3, the appliance 1 itself can have the form of a pair of tongs 5 which is hand-operated and which has one fixed and one movable leg 6 and 7 and two jaws 8 and 9 which are movable towards and away from each other. When moving the jaws 8, 9 towards each other by manually pressing the legs 6, 7 together and using a driving means 10, which will be described below, the sleeve 4 is crimped against the hose 2, thereby sealing the same.

Figure 2:
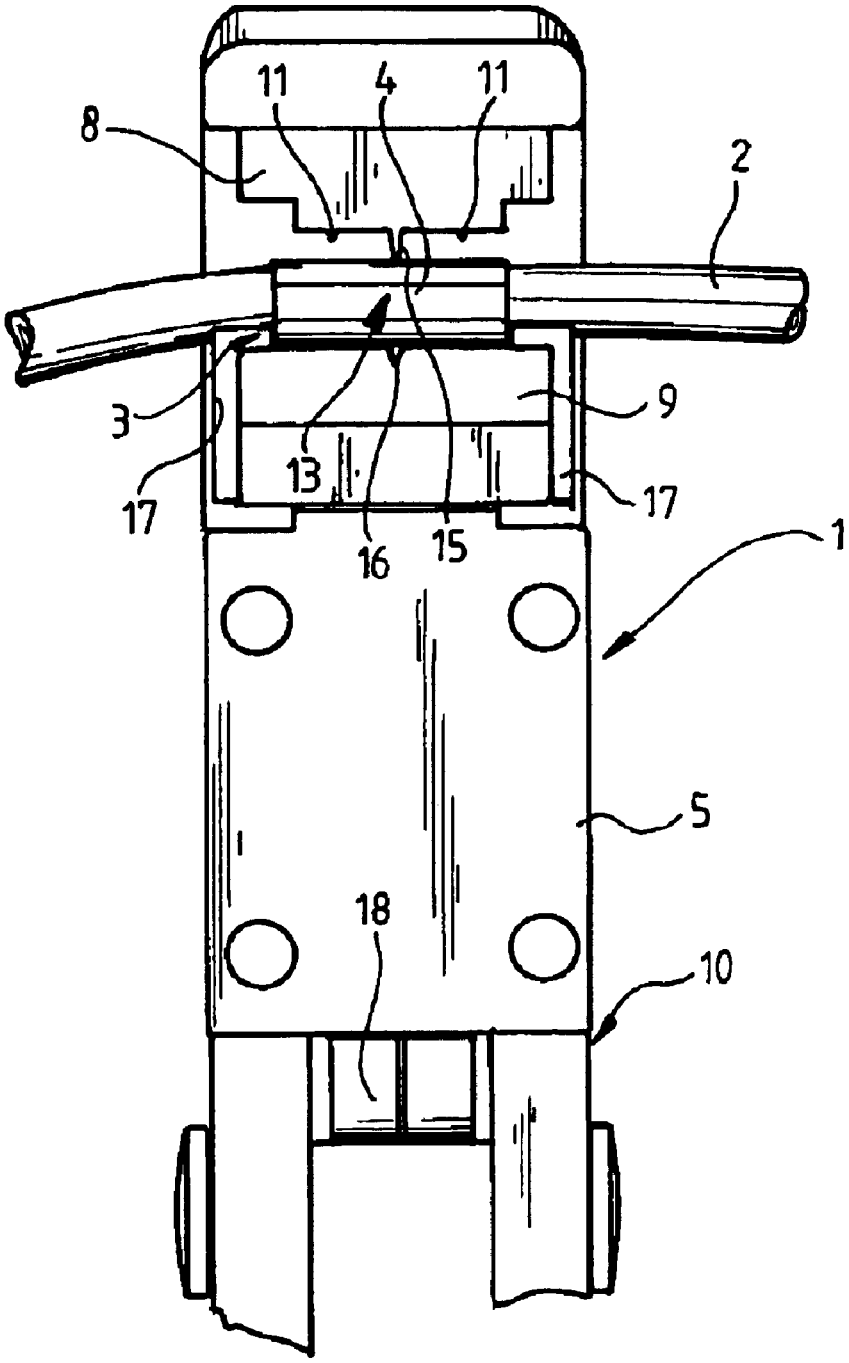
FIG. 2 is a front view of a part of the appliance according to FIG. 1 in the initial position.

More specifically, as best seen in FIG. 2, at least one of the jaws 8 or 9, in this case the jaw 8, has at least one bar 11 which projects towards the other jaw 9 or 8, in this case the jaw 9. In the above-described movement of the jaws 8, 9 towards each other, this bar 11 makes a marked indentation 12, se FIGS. 4, 5A and 5B, in the sleeve 4 and in the hose 2. In the preferred embodiment, there are two such bars 11, which are placed substantially in parallel at a distance from each other and extend substantially transversely of the longitudinal direction of the sleeve 4. The bars 11 are preferably straight and make two substantially transverse indentations 12 in the sleeve 4 and in the hose 2 to reinforce the sealing thereof as well as the fixing of the sleeve 4 on the hose 2. If desired and if suitable, there may, of course, be more than two such bars 11 or bars which are differently placed/formed on said jaw 8.

Figure 4:
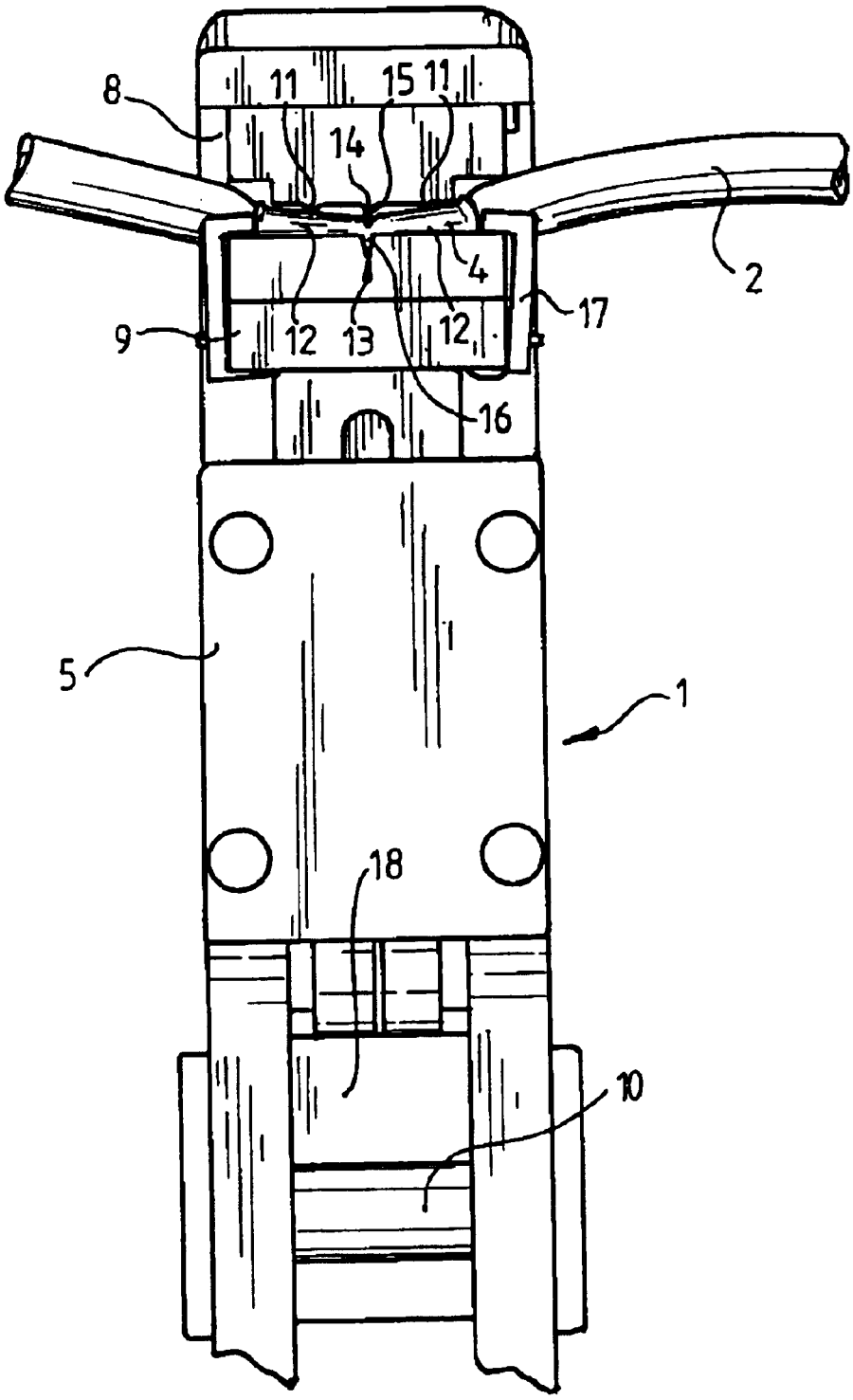
FIG. 4 is a view corresponding to FIG. 2, the appliance being in the end position.

Moreover, at least one of the jaws 8 or 9, also in this case the jaw 8, has a cutting means 13 projecting towards the other jaw 9 or 8 (see FIGS. 2 and 4). When the jaws 8, 9 are moving towards each other in the described manner, this cutting means 13 makes a cutting indication 14 in the sleeve 4 and in the hose 2 to allow the sleeve and the hose to be cut in a sealing manner.

In the shown embodiment, the cutting means 13 is preferably formed as a substantially straight cutting edge 15. The cutting edge extends substantially transversely of the longitudinal direction of the sleeve 4 and thus makes a substantially transverse cutting indication 14 in the sleeve 4 and in the hose 2. As seen in FIGS. 2 and 4, the cutting edge 15 projects to greater extent than the bars 11 and suitably co-operates with an opposite, straight recess 16 in the opposite jaw, in this case the jaw 9. The depth, width and form of the recess 16 can vary, and the recess is suitably adapted to the form of the cutting edge 15 and to the qualities of the material of the hose 2 and the sleeve 4. In certain applications, the recess 16 can, if required or desired, be omitted.

Preferably, the cutting edge 15 is situated substantially halfway between the bars 11, if they are two in number, such as shown in FIGS. 2 and 4. If there are further bars 11, the cutting edge 15 is suitably placed halfway between two adjacent bars, preferably the ones situated closest to the middle. In a certain application, it is, of course, also possible to place the cutting edge 15 outside or on one side of the bar or the bars 11.

Figure 5A:
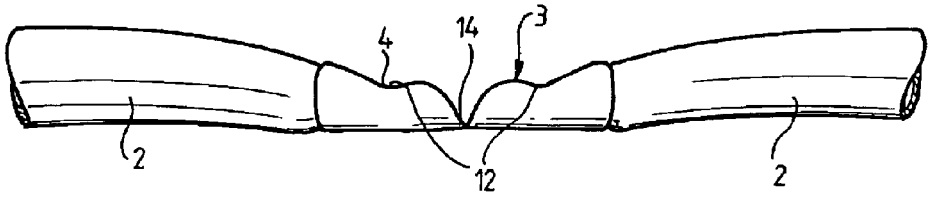
FIGS. 5A and 5B are side views which show the sealed hose, partially cut open, in a position after sealing and in a position after completed cutting of the hose.
Figure 5B:
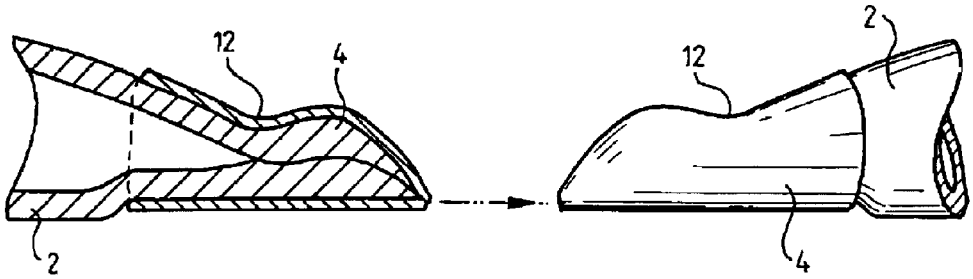

The cutting indication 14 mentioned above is preferably such that the sleeve 4 and the hose 2 are not cut or broken directly when sealing by means of the appliance 1, such as shown in FIG. 5A, but at an optional point of time after that. Then the sleeve 4 and the hose 2 are separated along the cutting indication 14 by manual or mechanical bending back and forth, until the sleeve is divided by fatigue fracture, as shown in FIG. 5B.

Naturally, nothing prevents the sleeve 4 and the hose 2 from being separated along the cutting indication 14 directly in connection with the actual sealing.

To fix the sleeve 4 and the hose 2 in the intended position between the jaws 8 and 9 in the appliance 1 when sealing, at least one of the jaws 8 or 9, in this case the jaw 9, has a fixture 17. The fixture fixes and supports the hose 2 and the sleeve 4 laterally, horizontally and vertically and can be formed in an optional manner which is not described in further detail.

For practical and other reasons, in the disclosed and described embodiment the bars 11 and the cutting edge 15 are arranged on one of the jaws 8 or 9, in this case the jaw 8, and the fixture 17 on the other, opposite jaw 9 or 8, in this case the jaw 9. The bars 11, the cutting edge 15 and the fixture 17 can be mounted on the associated jaw 8, 9 with the aid of suitable attachment means, which are not shown. Alternatively, one/some of or all these components can be made in one piece with the associated jaw. In the shown case, the bars 11 and the cutting edge 15 are made in one piece with the associated jaw, whereas the fixture 17 is mounted on the associated jaw, see FIGS. 2 and 4.

In the preferred embodiment, the jaw 8 provided with the bars 11 and the cutting edge 15 suitably has the form of a die is which is fixedly mounted in the appliance 1 with the aid of attachment means (not shown), see FIGS. 2 and 4. In a corresponding manner, the jaw 9 provided with the fixture 17 has the form of a punch. This punch is mounted in a slidable manner (not shown) in the appliance 1 and is actuatable by the previously mentioned driving means 10. The driving means 10 suitably consists of a gear generally designated 18, which can be an eccentric mechanism or the like and which is suitably connected to and actuatable by means of the movable leg 7 of the pair of tongs 5.

The invention is not, of course, limited to the embodiment which is described above and shown in the drawings, and can be modified in many different ways within the scope of protection according to the appended claims.

The appliance 1 does not, for example, need to be a manually operable pair of tongs, but it can alternatively be a separate tool or a tool which is included in a machine and driven electrically, pneumatically, hydraulically etc according to need and desire. The jaws 8, 9 with the associated components (bars 11, cutting edge 15 and fixture 17) can be attached to the appliance 1 in a replaceable manner and match the size of the hose 2 and the sleeve 4 and/or be mutually exchangeable etc.

What is claimed is:

[1. An appliance for mechanical sealing of hollow hoses (2) of elastic material with a sealing means (3) which is made of plastically deformable material and which is applied to the hose, said appliance (1) having two jaws (8, 9), at least one of the jaws is movable towards and away from the other jaw and the jaws crimp the sealing means (3) against the hose (2) to seal the same, characterised in that the sealing means (3) has the form of a sleeve (4) which is slipped on to the hose (2), that at least one of the jaws (8 or 9) has at least one straight bar (11) having a projecting end which projects towards the other jaw (9 or 8) and which, when at least one the jaws is moving towards the other jaw, makes an indentation (12) in the sleeve (4) and the hose (2) to reinforce the sealing thereof as well as the fixing of the sleeve on the hose, that at least one of the jaws (8 or 9) has a cutting means (13), which projects towards the other jaw (9 or 8) and which when at least one of the jaws (8, 9) is moving towards the other jaw, makes a cutting indication (14) in the sleeve (4) and the hose (2) to allow a sealing cutting of the hose (2), and that the cutting means (13) has the form of a substantially straight cutting edge (15) which projects to a greater extent than the projecting end of said at least one bar (11).]

[2. An appliance according to claim 1, characterized in that there are at least two straight bars (11) having projecting ends which are arranged substantially in parallel at a distance from each other and extend substantially transversely of the longitudinal direction of the sleeve (4) to make a corresponding number of substantially transverse indentations (12) in the sleeve (4) and the hose (2), and that the cutting means (13) extends substantially transversely of the longitudinal direction of the sleeve (4) and makes a substantially transverse cutting indication (14) in the sleeve (4) and the hose (2).]

[3. An appliance according to claim 2, characterized in that the cutting means (13) has the form of a substantially straight cutting edge (15), which projects to a greater extent than the projecting ends of the at least two straight bars (11).]

[4. An appliance according to claim 3, characterized in that the cutting edge (15) cooperates with an opposite recess (16) in the other jaw (9 or 8) and is situated substantially halfway between two adjacent bars (11);

at least one of the jaws (8 or 9) has a fixture (17) to position the sleeve (4) and the hose (2) between the jaws (8, 9);

the bars (11) and the cutting edge (15) are situated on one jaw (8) and that the fixture (17) is situated on the other jaw (9), the bars, the cutting edge and the fixture being mounted on or being make in one piece with the associated jaw, the jaw (8) provided with the bars (11) an the cutting edge (15) has the form of a die, which is fixedly mounted in the appliance (1) and the jaw (9) provided with the fixture (17) has the form of a punch, which is movably arranged in the appliance (1) and actuatable by a driving means (10); and the appliance has the form of a pair of tongs (5) which is hand operated and has one fixed and one movable leg (6, 7), the movable leg (7) actuating the jaw (9) forming the punch by means of a gear drive.]

[5. An appliance according to claim 3, characterized in that the cutting edge (15) cooperates with an opposite recess (16) in the other jaw (8 or 9);

the cutting edge (15) is situated on one side of the bars (11);

at least one of the jaws (8 or 9) has a fixture (17) to position the sleeve (4) and the hose (2) between the jaws (8, 9);

the bars (11) and the cutting edge (15) are situated on one jaw (8) and the fixture (17) is situated on the other jaw (9), the bars, the cutting edge and the fixture being mounted on or being made in one piece with the associated jaw;

the jaw (8) provided with the bars (11) and the cutting edge (15) has the form of a die, which is fixedly mounted in the appliance (1) and the jaw (9) provided with the fixture (17) has the form of a punch, which is movably arranged in the appliance (1) and actuatable by driving means (10); and the appliance has the form of a pair of tongs (5) which is hand operated and has one fixed and one movable leg (6, 7), the movable leg (7) actuating the jaw (9) forming the punch by means of a gear device.]

[6. An appliance according to claim 2, characterized in that at least one of the jaws (8 or 9) has a fixture (17) to position the sleeve (4) and the hose (2) between the jaws (8, 9).]

[7. An appliance according to claim 2, characterized in that the at least two bars (11) and the cutting edge (15) are situated on one jaw (8), and that the fixture (17) is situated on the other jaw (9), at the least one bar, the cutting edge and the fixture being mounted on or being make in one piece with the associated jaw.]

[8. An appliance according to claim 1, characterized in that the cutting edge (15) co-operates with an opposite recess (16) in the other jaw (9 or 8).]

[9. An appliance according to claim 8, characterized in that the cutting edge (15) is situated substantially half-way between two adjacent bars (11).]

[10. An appliance according to claim 8, characterized in that the cutting edge (15) is situated on one side of the at least one bar (11).]

[11. An appliance according to claim 8, characterized in that at least one of the jaws (8 or 9) has a fixture (17) to position the sleeve (4) and the hose (2) between the jaws (8, 9).]

[12. An appliance according to claim 1, characterized in that the cutting edge (15) is situated substantially half-way between two adjacent bars (11).]

[13. An appliance according to claim 1, characterized in that the cutting edge (15) is situated on one side of the at least one bar (11).]

[14. An appliance according to claim 1, characterized in that at least one of the jaws (8 or 9) has a fixture (17) to position the sleeve (4) and the hose (2) between the jaws (8, 9).]

[15. An appliance according to claim 14, characterized in that the at least one bar (11) and the cutting edge (15) are situated on one jaw (8), and that the fixture (17) is situated on the other jaw (9), the at least one bar, the cutting edge and the fixture being mounted on or being made in one piece with the associated jaw.]

[16. An appliance according to claim 15, characterized in that the jaw (8) provided with the at least one bar (11) and the cutting edge (15) has the form of a die, which is fixedly mounted in the appliance (1), and that the jaw (9) provided with the fixture (17) has the form of a punch, which is movably arranged in the appliance (1) and actuatable by a driving means (10).]

[17. An appliance according to claim 16, characterized in that it has the form of a pair of tongs (5) which is hand-operated and has one fixed and one movable leg (6, 7), the movable leg (7) actuating the jaw (9) forming the punch by means of a gear device, preferably an eccentric mechanism or the like, forming the driving means (10).]

[18. An appliance for mechanical sealing of hollow hoses (2) of elastic material with a sealing means (3) which is made of plastically deformable material and which is applied to the hose, said appliance (1) having two jaws (8, 9), both of the jaws are movable towards and away from each other and which, when moving towards each other, crimp the sealing means (3) against the hose (2) to seal the same, characterised in that the sealing means (3) has the form of a sleeve (4) which is slipped on to the hose (2), that at least one of the jaws (8 or 9) has at least one straight bar (11) having a projecting end which projects towards the other jaw (9 or 8) and which, when the jaws (8, 9) are moving towards each other, makes an indentation (12) in the sleeve (4) and the hose (2) to reinforce the sealing thereof as well as the fixing of the sleeve on the hose, that at least one of the jaws (8 or 9) and which, when the jaws (8, 9) are moving towards each other, makes a cutting indication (14) in the sleeve (4) and the hose (2) to allow a sealing cutting of the hose (2), and that the cutting means (13) has the form of a substantially straight cutting edge (15), which projects to a greater extent than the projecting end of said at least one bar (11).]

*19. A process for sealing and allowing separation of a hollow hose of elastic material between, and capable of fluid communication with, a process container and a collecting vessel, comprising:*

*placing the hollow hose of elastic material, having a sealing device applied to a portion of the hose, between two jaws of a hand-held appliance, the two jaws capable of being moved relative to each other, at least one of the jaws configured to create an indentation in the hose with the sealing device, and at least one of the jaws supporting a cutting indication projection that projects towards the other jaw;*

*causing relative movement of the jaws towards each other to make an indentation in the hose with the sealing device to reinforce the sealing of the hose and fixing the sealing device on the hose; and*

*cutting transversely through the hose with the cutting indication projection,*

*wherein the indentation and the cut are formed without longitudinal relative movement between the hand-held appliance and the hollow hose.*

*20. The process of claim 19, further comprising making at least two substantially transverse indentations in the sealing device and hose with at least two bars extending along a straight line and disposed on the jaws, wherein the at least two bars are configured to create the indentation, and are arranged substantially in parallel at a distance from each other, and extend substantially transversely to the longitudinal direction of the sealing device, wherein each bar has a projecting end that projects towards an opposite jaw.*

*21. The process of claim 19, further comprising positioning the sealing device and the hose between the jaws with a fixture, the fixture being disposed on at least one of the jaws.*

*22. The process of claim 21, wherein at least one bar configured to create the indentation and the cutting indication projection are situated on one jaw, and the fixture is situated on the other jaw, wherein the bar projects towards an opposite jaw.*

*23. The process of claim 19, wherein the cutting indication projection co-operates with an opposite recess in the other jaw.*

*24. The process of claim 19, wherein the cutting indication projection is disposed on the same jaw as a bar that projects toward an opposite jaw.*

*25. The process of claim 19, wherein the cutting indication projection projects past a projecting end of at least one bar that projects towards the opposite jaw and is configured to create the indentation.*

*26. The process of claim 19, further comprising making a complete cut in the hose and the sealing device.*

*27. The process of claim 19, wherein a bar is rigidly coupled to a jaw, and the bar projects toward the opposite jaw and is configured to create the indentation in the hose with the sealing device when the jaws are moved toward each other.*

*28. The process of claim 19, wherein the sealing device comprises metal.*

*29. The process of claim 19, wherein only one jaw moves.*

*30. The process of claim 19, wherein relative movement of the jaws towards each other is caused manually.*

*31. The process of claim 19, wherein the sealing device surrounds a portion of the hose.*

*32. A process for sealing and allowing separation of a hollow hose of elastic material between, and capable of fluid communication with, a process container and a collecting vessel, comprising:*

*placing the hollow hose of elastic material, having a sealing device applied to a portion of the hose, between two jaws of a hand-held appliance, the two jaws capable of being moved relative to each other, at least one of the jaws configured to cause a projecting bar to create an indentation in the hose with the sealing device, and at least one of the jaws supporting a cutting indication projection that projects towards the other jaw;*

*causing relative movement of the jaws towards each other to make an indentation in the hose with the sealing device to reinforce the sealing of the hose and fixing the sealing device on the hose; and*

*cutting transversely through the hose with the cutting indication projection,*

*wherein the indentation and the cut are formed without longitudinal relative movement between the hand-held appliance and the hollow hose.*

*33. The process of claim 19, wherein the hose connects to the process container by way of a device adapted for introduction and/or withdrawal of a medium from the process container.*

*34. A process for sealing and allowing separation of a hollow hose of elastic material between, and capable of fluid communication with, a process container and a collecting vessel, comprising:*

*placing the hollow hose of elastic material, having a sealing device applied to a portion of the hose, between two jaws of a hand-held appliance, the two jaws capable of being moved relative to each other, at least one of the jaws supporting a cutting indication projection that projects towards the other jaw, wherein the cutting indication projection is disposed between two bars that project towards an opposite jaw and are configured to create indentations in the hose;*

*causing relative movement of the jaws towards each other to make an indentation in the hose with the sealing device to reinforce the sealing of the hose and fixing the sealing device on the hose; and*

*cutting transversely through the hose with the cutting indication projection,*

*wherein the indentation and the cut are formed without longitudinal relative movement between the hand-held appliance and the hollow hose.*

* * * * *